(12) United States Patent
Alboresi et al.

(10) Patent No.: US 6,177,677 B1
(45) Date of Patent: Jan. 23, 2001

(54) SYSTEM FOR STERILIZING MEDICINAL PRODUCTS BY BETA-RADIATION PROCESSING

(75) Inventors: Luigi Alboresi; Marco Santi, both of Modena (IT)

(73) Assignee: Hospal AG, Basel (CH)

( * ) Notice: Under 35 U.S.C. 154(b), the term of this patent shall be extended for 0 days.

(21) Appl. No.: 09/125,229

(22) PCT Filed: Dec. 16, 1997

(86) PCT No.: PCT/IB97/01570

§ 371 Date: Apr. 13, 1999

§ 102(e) Date: Apr. 13, 1999

(87) PCT Pub. No.: WO98/26805

PCT Pub. Date: Jun. 25, 1998

(30) Foreign Application Priority Data

Dec. 17, 1996 (IT) .............................................. TO96A1037

(51) Int. Cl.⁷ .................................................. G01N 21/00
(52) U.S. Cl. .................................... 250/453.11; 250/492.1
(58) Field of Search .......................... 250/453.11, 454.11, 250/492.1

(56) References Cited

U.S. PATENT DOCUMENTS

| | | |
|---|---|---|
| 3,224,562 * | 12/1965 | Bailey et al. .................... 250/453.11 |
| 3,264,473 | 8/1966 | Levin et al. . |
| 3,452,195 * | 6/1969 | Brunner ........................... 250/454.11 |
| 4,018,348 * | 4/1977 | Bosshard ......................... 250/453.11 |
| 4,020,354 * | 4/1977 | Fausse et al. .................... 250/453.11 |
| 5,396,074 * | 3/1995 | Peck et al. ....................... 250/454.11 |
| 5,400,382 * | 3/1995 | Welt et al. ....................... 250/454.11 |
| 5,904,897 * | 5/1999 | Kendall et al. ......................... 422/28 |

FOREIGN PATENT DOCUMENTS

| | | |
|---|---|---|
| 764337 | 12/1956 | (GB) . |
| 1 525 484 | 9/1978 | (GB) . |

* cited by examiner

*Primary Examiner*—Bruce C. Anderson
(74) *Attorney, Agent, or Firm*—Finnegan, Henderson, Farabow, Garrett & Dunner, L.L.P.

(57) ABSTRACT

A system is provided for sterilizing, by irradiation, a plurality of products, each product having an identification code. The products are carried on product carriers which include a carrier identification code. The system includes a product loading station, a product unloading station, an irradiation blocking containment, and an irradiation station location located within the containment. A conveyor passes from the loading station through the containment to the unloading station. Code readers are located along the conveyor for detecting and reading both the product identification code and the carrier identification code. A control and monitoring circuit receives the codes, and stores in memory an association between specific carriers and the products located on those carriers.

17 Claims, 12 Drawing Sheets

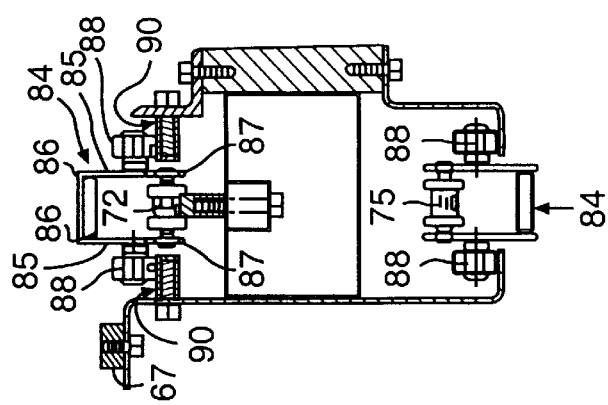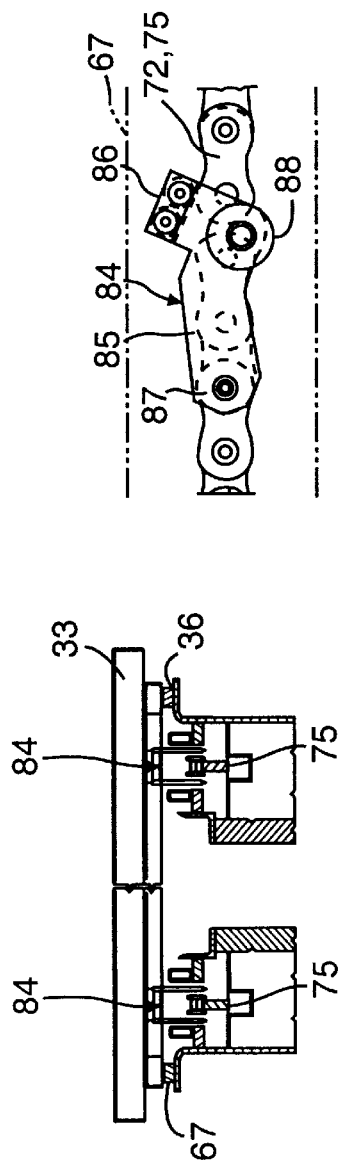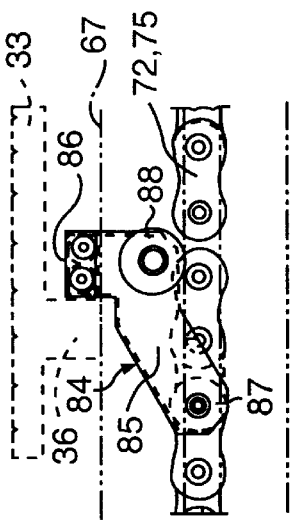

SYSTEM FOR STERILIZING MEDICINAL PRODUCTS BY BETA-RADIATION PROCESSING

BACKGROUND OF THE INVENTION

1. Field of the Invention

The present invention relates to an installation for the sterilization of medical products by irradiation.

2. Description of Related Art

It is known that tubes for extra-corporeal blood circulation, known as blood lines, which are used for extra-corporeal blood treatment, such as haemodialysis, undergo a sterilization process aimed at ensuring the complete elimination of germs. At the present time, this sterilization is carried out in various ways, for example by gamma-ray irradiation. However, this technique has various disadvantages linked to the dangerous nature of the material used for generating radiation, to the cost of shielding the irradiation equipment and to the difficulty in obtaining the official permits necessary for using it, in view of the growing awareness of environmental pollution. Moreover, high-temperature steam sterilization is unsuitable for PVC blood lines since, to ensure appropriate sterilization, it is necessary to employ a temperature near the softening point of PVC, thus entailing the risk of damage to the products.

At the present time, for further types of product, other irradiation methods are adopted, such as beta-ray irradiation, which do not cause the problems mentioned above. Beta-ray sterilization is, for example, used, with good results, for treating edible products or medical products of a non-critical nature.

However, where PVC blood lines are concerned, this sterilization treatment has not yet been used on a large scale due to the critical nature of the material and the stringent sterilization requirements demanded for such a use. In fact, on the one hand, the chemical and physical characteristics of PVC are extremely sensitive to irradiation doses and set strict upper limits to the doses which can be used and, on the other hand, the need for sufficient sterilization sets lower limits on these doses. Furthermore, irradiation installations which have not been designed specifically (such as third-party servicing installations) do not make it possible to ensure sufficient sterilization of the product as a whole, without some of the product being subjected to excessive exposure. In addition to this, the low unit price of the product makes it impossible to employ costly monitoring and management techniques if the competitiveness of blood lines sterilized by beta rays, as compared with lines sterilized by conventional methods, is to be maintained.

SUMMARY OF THE INVENTION

The object of the present invention is to provide a sterilization installation which makes it possible to sterilize fragile products, such as PVC blood lines, efficiently and economically, without in any way damaging them.

In order to achieve this object, according to the invention an installation for the sterilization of medical products by irradiation is provided, characterized in that it comprises:

at least one product loading station, at least one product unloading station, an irradiation station located inside a containment having walls capable of stopping sterilizing radiation, conveyance means for conveying the products to be sterilized from the loading station to the irradiation station and the sterilized products from the irradiation station to the unloading station, the conveyance means comprising grouping means for grouping the products to be sterilized in the vicinity of the irradiation station.

Advantageously, the grouping means comprise a first conveyor and a second conveyor, the second conveyor being located immediately downstream of the first conveyor in relation to the direction of conveyance of the products and having a conveying speed lower than the conveying speed of the first conveyor.

According to a characteristic of the invention, the first and second conveyors comprise retractable drive members for catching the products and strictly subjecting their displacement to that of the corresponding conveyor.

According to a characteristic of the invention, the second conveyor comprises two half-conveyors separated by a gap located in a zone, towards which the irradiation station emits the sterilizing radiation.

According to a characteristic of the invention, the installation comprises a third conveyor located immediately downstream of the second conveyor in relation to the direction of conveyance of the products, the third conveyor having a conveying speed higher than the conveying speed of the second conveyor.

According to a characteristic of the invention, the conveyance means comprise superposed conveyance sections, the conveyance sections located at a first level conveying the products to be sterilized from the loading station to the irradiation station and the conveyance sections located at a second level conveying the sterilized products from the irradiation station to the unloading station.

a vertical transporter for transferring the products from one conveyance level to the other conveyance level.

According to a characteristic of the invention, the installation comprises means for the detection of products, said detection means being arranged along the conveyance means, and control and monitoring means connected to the detection means in order to follow the travel of the products on the conveyance means.

According to a characteristic of the invention, the installation comprises a plurality of trays intended for supporting the products on the conveyance means, each tray being provided with an identification code, the means for the detection of products comprising code-reading means capable of reading the code affixed to each tray.

According to a characteristic of the invention, the means for the detection of products comprise code-reading means capable of reading an identification code affixed to each of the products arranged on each tray, and the control and monitoring unit is provided for combining and storing the identification code of each product and the identification code of the tray supporting this product.

According to a characteristic of the invention, the means for the detection of products comprise mechanical travel-limit detection means arranged inside the containment, in order to detect the position of the trays inside the containment and transmit a corresponding signal to the control and monitoring unit.

According to a characteristic of the invention, the invention comprises means for measuring the speed of the second conveyor which are connected to the control and monitoring means, and the control and monitoring means are provided for setting the irradiation emitted by the irradiation station as a function of the speed variations of the conveyor in such a way that the products receive a predetermined irradiation dose.

Another subject of the invention is a method for the sterilization of medical products by irradiation, comprising the steps of:

placing at least one product provided with a product identification code onto a tray provided with a tray identification code, reading the tray identification code and the product identification code, storing the combination of the tray and product identification codes, conveying the tray along a definite path towards an irradiation station, and locating the tray by reading the tray identification code at definite places along the path.

BRIEF DESCRIPTION OF THE DRAWINGS

Other advantages and characteristics of the invention will emerge from a reading of the following description. Reference will be made to the accompanying drawings, in which:

FIG. 12 shows a detail of the conveyors of FIG. 11;

FIGS. 13 and 14 show side views, in two different positions, of the drive members of the conveyors of FIG. 11;

FIG. 15 shows a cross-section through part of the conveyors of FIG. 11;

DESCRIPTION OF PREFERRED EMBODIMENT

Figure 1:
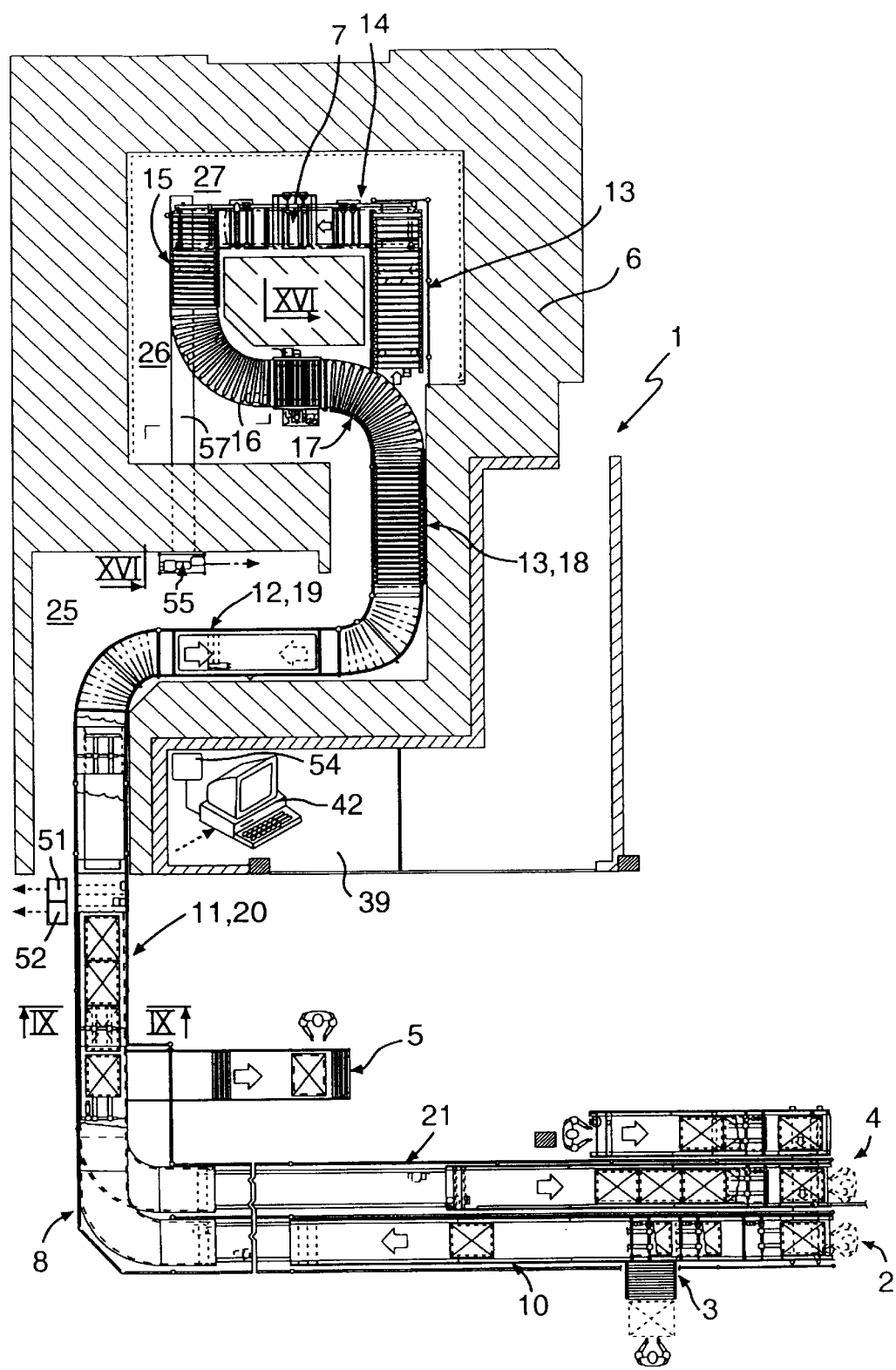
FIG. 1 shows a top view of the entire sterilization installation according to the invention.

Referring to FIG. 1, the sterilization installation 1 comprises a main loading station 2, an auxiliary loading station 3, a main unloading station 4, an auxiliary unloading station 5, a containment or bunker 6, an irradiation station 7 located inside the containment 6, and conveyance means 8 connecting the loading station 2 to the unloading station 4.

The conveyance means 8 comprise a plurality of conveyors, preferably of the roller type, with sections for the conveyance of products to be sterilized and sections for the conveyance of sterilized products, the said sections being superposed. In particular, the conveyance means 8 comprise the following successive sections:

a first section 10 arranged in the extension of the main loading station 2, a second section 11 perpendicular to the first section 10, a third section 12 perpendicular to the second section 11 and extending in a direction opposite to that of the first section 10, a fourth section 13 perpendicular to the third section 12 and extending in the same direction as the second section 11, a fifth section 14, passing through the irradiation station 7, perpendicular to the fourth section 13 and extending in a direction opposite to that of the third section 12, a sixth section 15 perpendicular to the fifth section 14 and extending in a direction opposite to that of the fourth section 13, a seventh section 16 of curved shape, with its concavity facing towards the irradiation station 7, an eighth station 17 of curved shape, with its concavity facing the opposite way to the irradiation station 7, this eighth section 17 being in a plane located below a parallel plane containing the seven preceding sections, a ninth section 18, a tenth section 19 and an eleventh section 20 extending respectively below the fourth section 13, the third section 12 and the second section 11, and a twelfth section 21 parallel to the first section 10 and extended by the main unloading station 4.

In other words, the sections 13 to 17 form a ring inside the containment 6 and are preceded and followed by superposed sections for conveying the boxes of products to be irradiated and irradiated boxes.

All the conveyance sections form an angle with one another, with the exception of sections 13 to 15, which are connected to one another by means of curved portions.

The containment 6 is produced from masonry, and it delimits three zones which communicate with one another:

a first entry and exit zone 25 containing part of the sections 11, 20, the sections 12, 19 and part of the sections 13, 18, an intermediate second zone 26 containing part of the sections 13, 18 and the sections 15 to 17, and a third zone 27 containing the section 14 and the irradiation station 7.

The third zone 27 does not contain any electrical or electronic equipment which could be damaged by the ionizing radiations generated in the irradiation station 7. Moreover, the mechanical members which are located there are produced from materials highly resistant to ionization, such as stainless steel, and lubricated by means of specific products.

Figure 6:
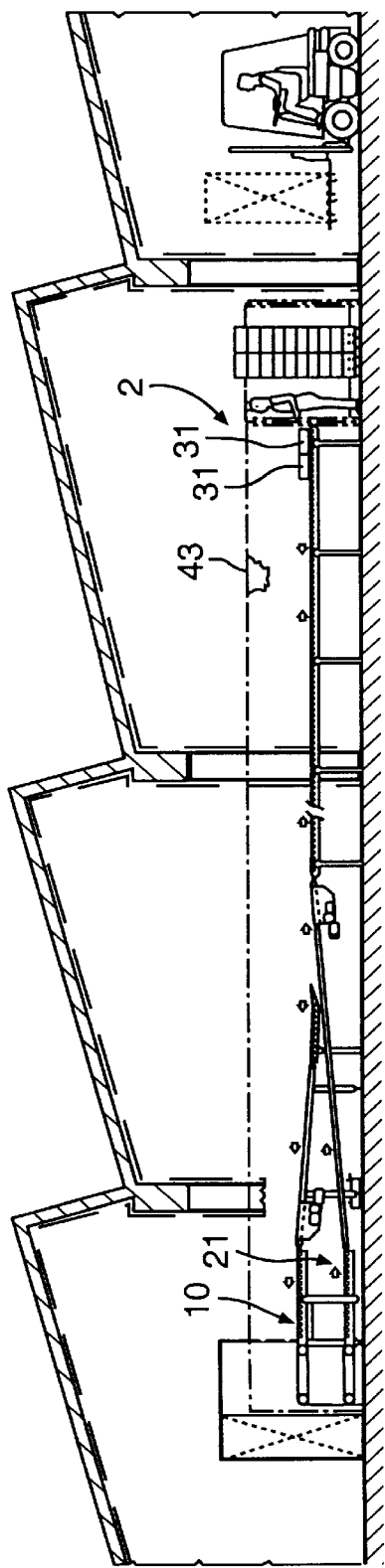
FIG. 6 shows a side view of part of the installation of FIG. 1.

Those sections of the conveyance means which are located outside the containment 6 are enclosed in a metal trelliswork cage 43 preventing access (see FIG. 6).

Figure 4:
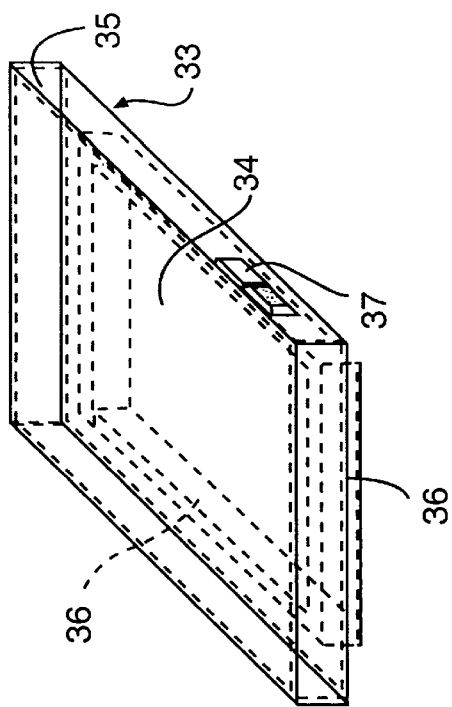
FIG. 4 shows a perspective view of a tray for transporting the two boxes of FIG. 3.
Figure 3:
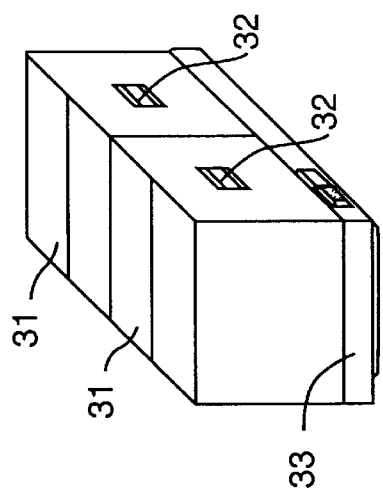
FIG. 3 shows a perspective view of two boxes, each containing a plurality of blood lines.
Figure 2:
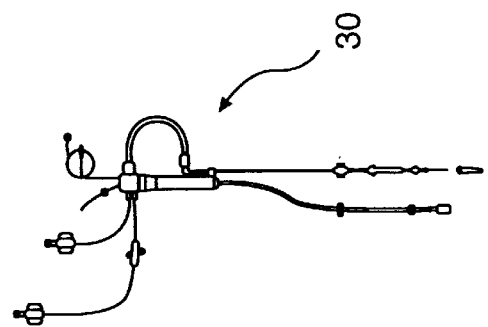
FIG. 2 shows diagrammatically a blood line for once-only use.

The installation 1 is intended for the sterilization of blood lines, for example of the type illustrated in FIG. 2 and identified by the reference numeral 30. A plurality of blood lines 30 are arranged in a box 31 (FIG. 3) provided with a box label 32 bearing a product identification code (for example, a bar code). Two boxes 31 are arranged side by side on a rectangular tray 33 (see, in particular, FIG. 4), preferably made of metal, which comprises a flat bottom 34 equipped with a peripheral rim 35. Fastened to the lower face of the bottom 34 is a frame 36, the sides of which are set back slightly relative to the corresponding rims of the bottom 34. A tray label 37 is glued to the rim 35 of the tray 34 and bears an identification code (typically, a number specific to the tray or a bar-code).

At the main loading station 2 (see FIG. 5) the trays 33 are loaded in such a way that the two boxes 31 advance one behind the other on the conveyance means. The main loading station 2 comprises a group of code readers 40, 41, 44 of the optical type which are arranged laterally relative to the conveyor and are oriented in such a way that each of them can read the identification code of the two boxes and the identification code of the tray from the respective labels 32, 37 and emit corresponding identification signals. The code readers 40, 41, 44, as well as the other code readers mentioned below, are connected to a control and monitoring unit 42 (see FIG. 1) located in a room 39 contiguous to the containment 6. The control and monitoring unit 42 is connected to a memory 54 and, if appropriate, to a processing unit, placed at a suitable location along the conveyance means 8, and to optical and/or acoustic signaling devices not illustrated in detail.

An auxiliary loading station 3 is arranged laterally relative to the first section 10 of the conveyance means. This auxiliary station 3 is provided with a code reader 45 for the label of a tray, the said code reader being intended to emit a corresponding code signal.

Figure 5:
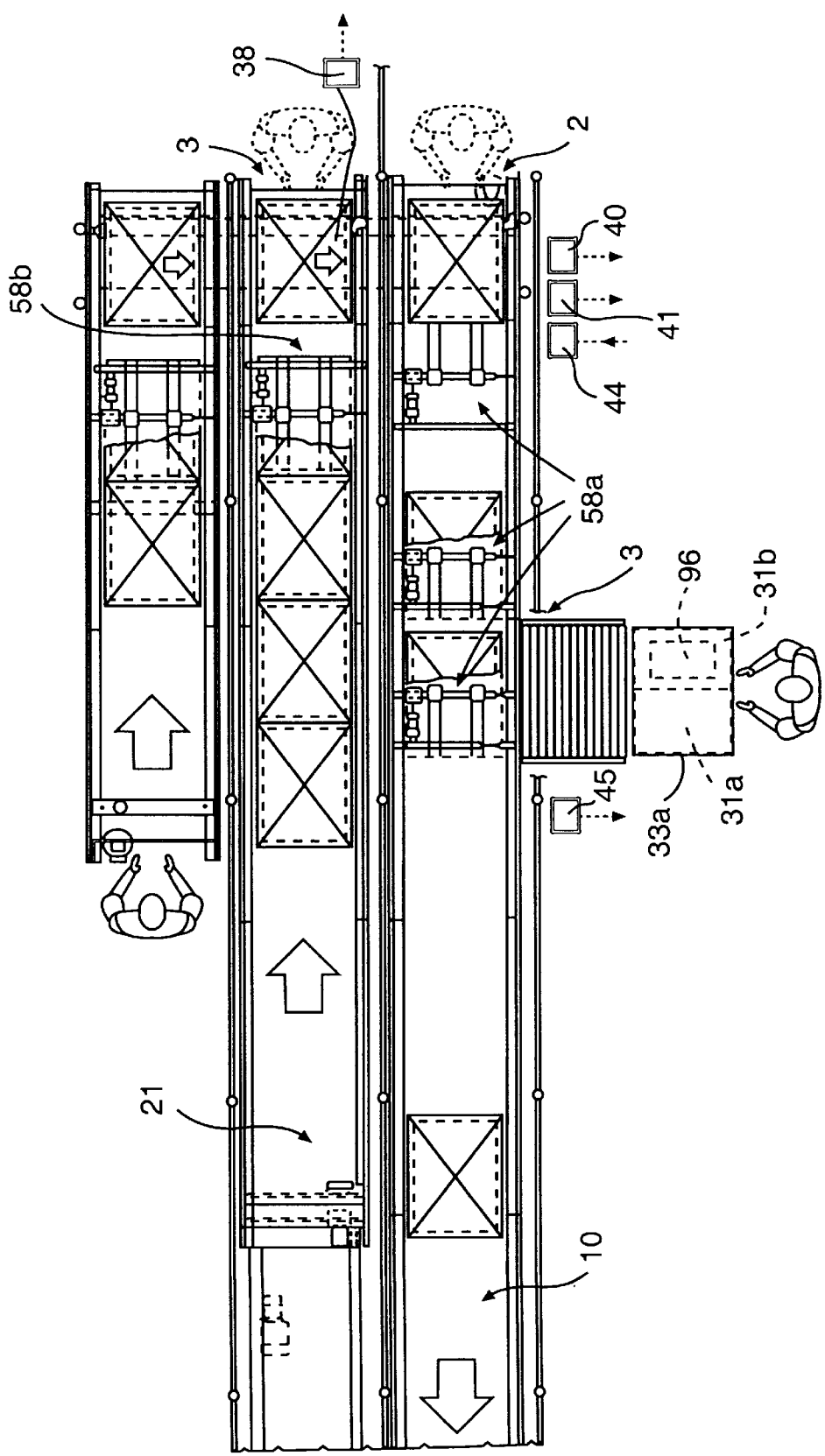
FIG. 5 shows an enlarged detail of FIG. 1.
Figure 7:
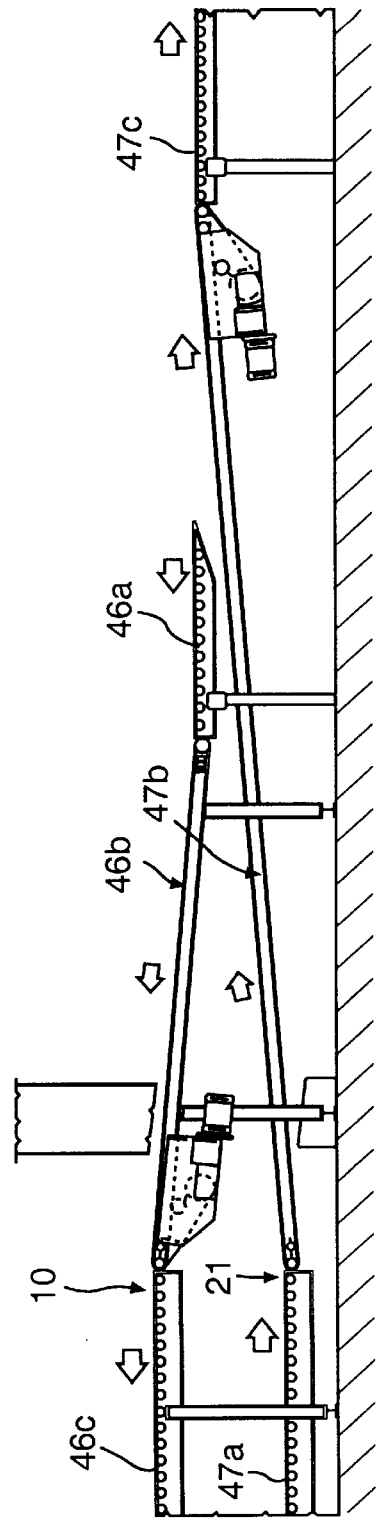
FIG. 7 shows an enlarged detail of FIG. 6.

As illustrated in FIGS. 5 to 7, the first and the twelfth conveyance sections 10 and 21 each comprise three different conveyors 46a, 46b, 46c, respectively, and 47a, 47b, 47c, each of them defining an initial path, an intermediate path and a final path in the respective conveying direction. Since the main loading station 2 and the main unloading station 4 are arranged side by side, the conveyors 46a and 47c are at the same level. The intermediate conveyors 46b, 47b define ramps which both ascend in the direction of travel of the trays 33. The conveyor 47a is arranged laterally relative to the conveyor 46c, at a lower level. The conveyors 46a and 47c are equipped with blocking devices 58a, 58b which are illustrated diagrammatically and are not described in detail. The main unloading station 4 comprises, furthermore, a code reader 38 arranged so as to make it possible to read the label 37 of the tray 33 reaching the end of its travel.

The sections 10 and 21 are connected to the contiguous sections 11, 20 by means of curved connecting portions 48, 49, respectively (see FIG. 8), in such a way that the sections 11 and 20 are exactly superposed.

Figure 8:
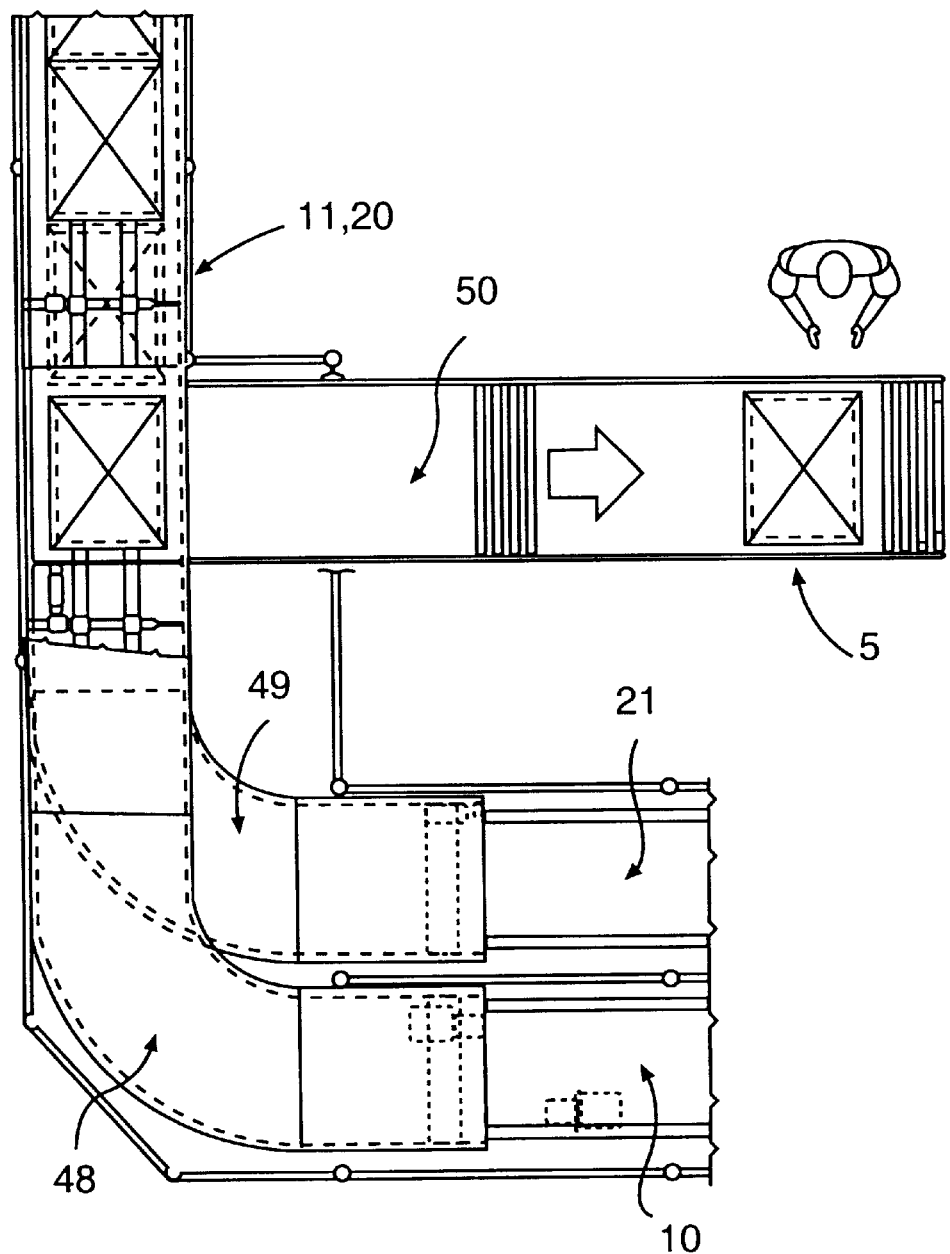
FIG. 8 shows another enlarged detail of FIG. 1.
Figure 9:
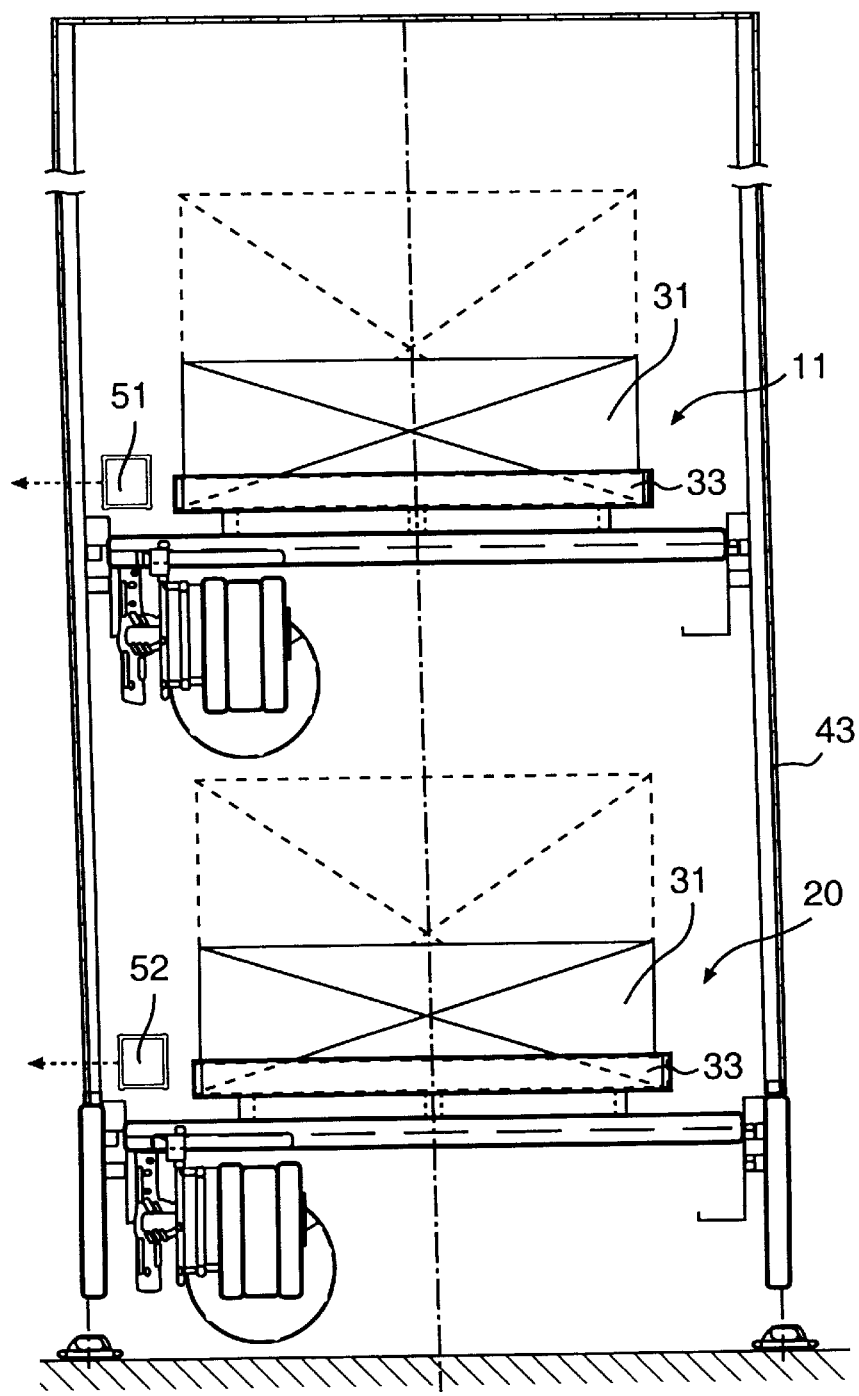
FIG. 9 shows a cross-section through the installation along the line IX—IX of FIG. 1.

As shown in detail in FIG. 8, the conveyance section 20 is connected to the auxiliary unloading station 5 by means of a junction section 50 perpendicular to the conveyance section 20. Each conveyance section 11, 20 is equipped with a respective code reader 51,52 (FIG. 1).

Inside the containment 6, the conveyors defining the section 14 are driven by means of a single motor 55 (see FIGS. 1 and 15) which is arranged in the entry and exit zone 25 and therefore outside the critical zone 27. The motor 55 is connected to the conveyors of the section 14 by means of a shaft 57 passing through a wall of the containment 6. The motor 55 comprises a pulse transmitter 56 which accurately controls the speed of the said motor and emits signals which are supplied to the control and monitoring unit 42, in order to check that the conveyor system is functioning correctly and, if appropriate, that the process parameters are appropriate.

Figure 10:
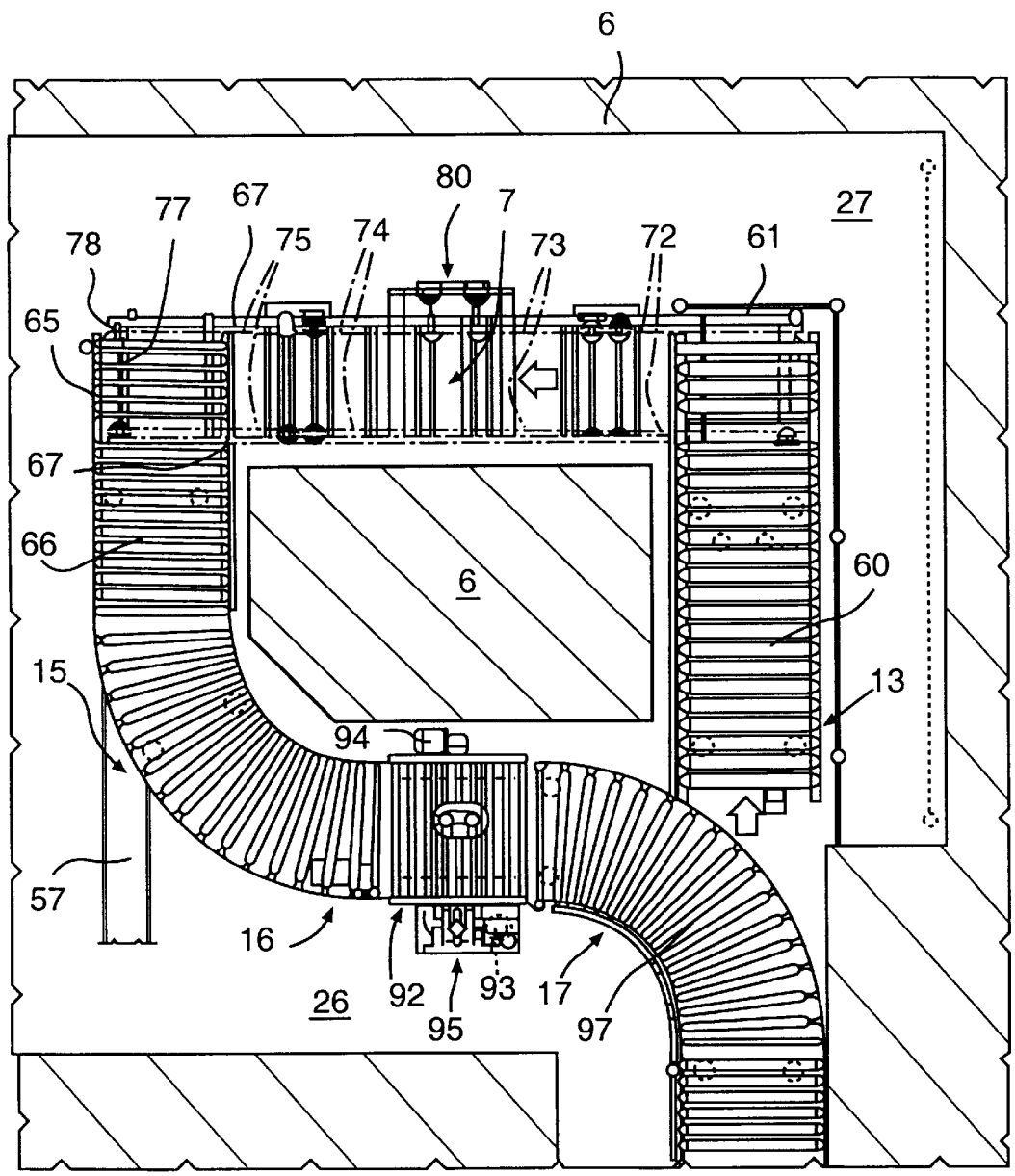
FIG. 10 shows another enlarged detail of FIG. 1.

The conveyance section 13 extending from the entry and exit zone 25 to the sterilization zone 27 comprises a stainless-steel roller conveyor 60 and, at its end contiguous to the section 14, a travel-limit detector 61 of the mechanical-arm type, shown diagrammatically in FIG. 10. The travel-limit detector 61 is connected to the control and monitoring unit 42 by means of a rod assembly and transducers.

The section 14 comprises three chain conveyors 62, 63, 64. The end conveyors 62 and 64 have a high conveying speed, whilst the speed of the central conveyor 63 is lower. Guide rails 67 are arranged on each side of the section 14, outside the chain conveyors 62 to 64, in order to support and guide the trays 33. A mechanical arm-type detector (not shown) is mounted level with the central conveyor 63 in order to detect the presence of the trays 33. A travel-limit detector 65 is mounted at that end of the conveyor 64 which is contiguous with the conveyance section 15, in order to detect the arrival of a tray 33 and trigger the functioning of the roller conveyor 66 of the conveyance section 15.

Figure 11:
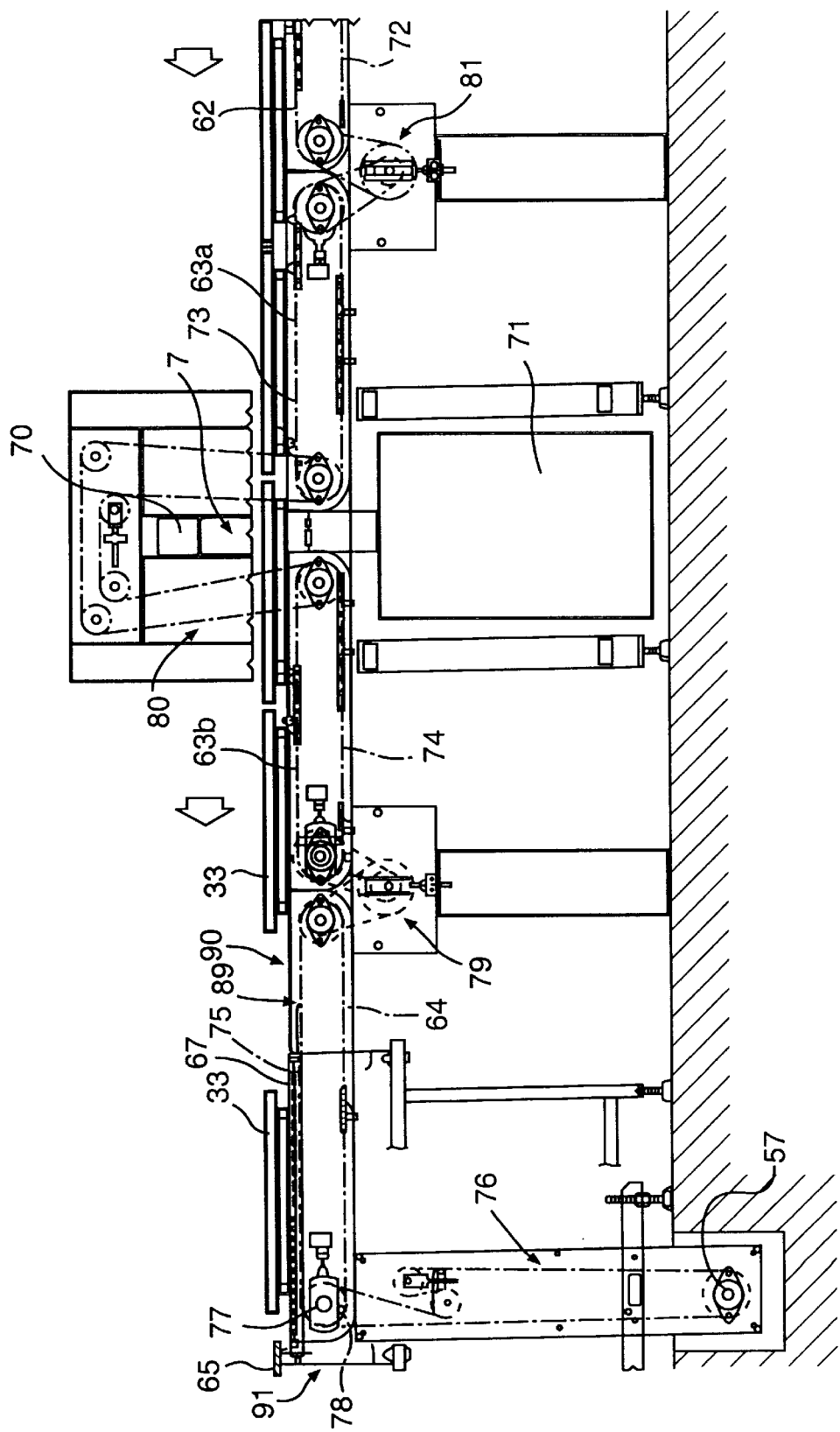
FIG. 11 shows a side view of part of the installation of FIG. 1.
Figure 16:
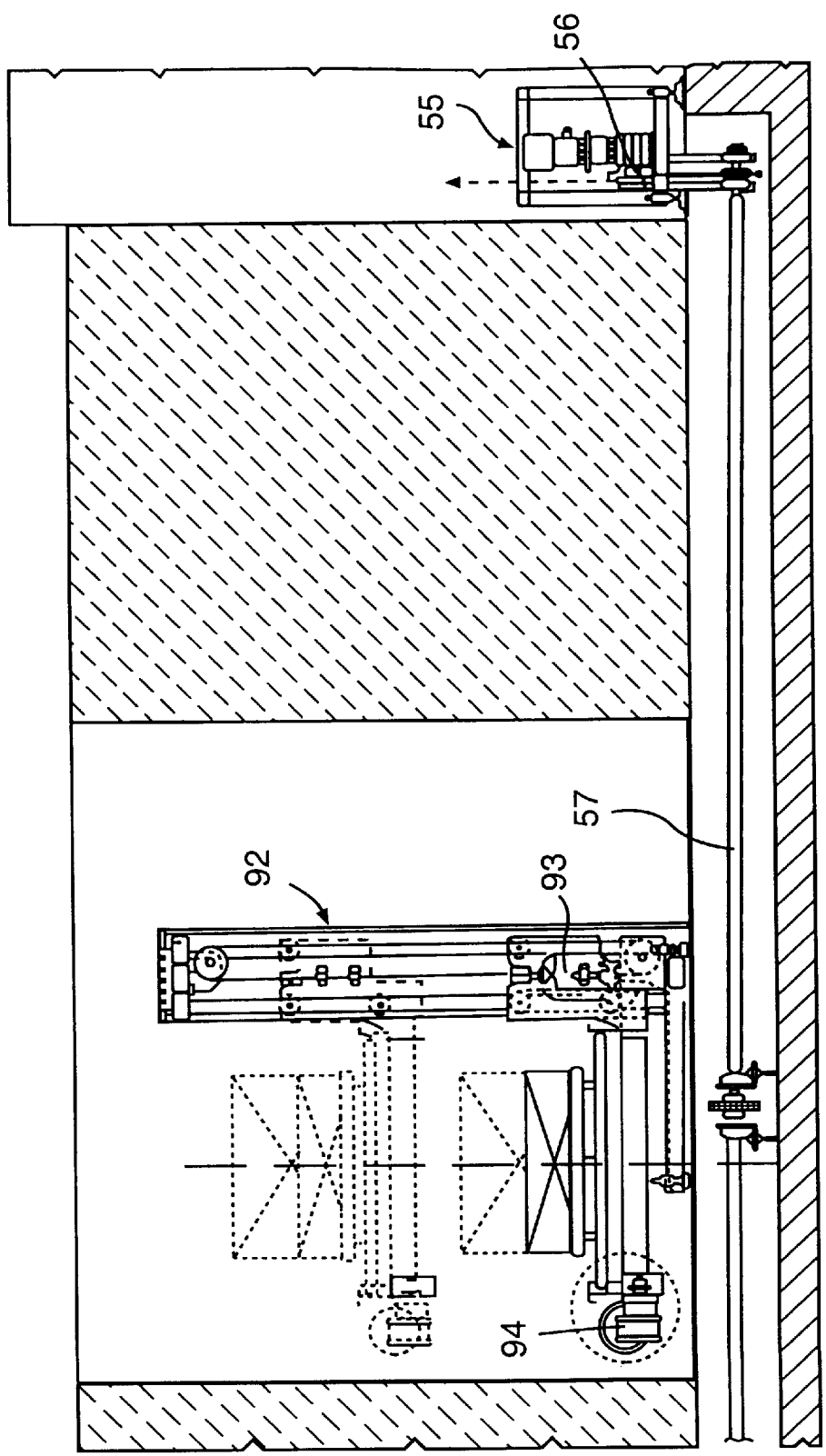
FIG. 16 shows a cross-section through the installation along the line XVI—XVI of FIG. 1.

As may be seen in FIG. 11, the central conveyor 63 comprises two half-conveyors 63a, 63b separated by a gap located in the irradiation station 7. This station comprises a particle accelerator 70 provided with a scanning head (not shown) which is arranged above the path of the products to be sterilized, vertically in line with the gap separating the two half-conveyors 63a, 63b, and an absorbing well 71 arranged vertically in line with the scanning head, below the level of the conveyors 63a, 63b, in order to absorb and dissipate the excess beta radiation energy.

As shown diagrammatically in FIGS. 10 and 11, the conveyor 62 consists of a pair of chains 72, the half-conveyor 63a consists of a pair of chains 73, the half-conveyor 63b consists of a pair of chains 74 and the conveyor 64 consists of a pair of chains 75. For actuating these conveyors, the shaft 57 drives the pair of chains 75 by means of a chain transmission 76, a drive shaft 77 and a gearwheel 78; the pair of chains 75 drives the pair of chains 74 by means of a reduction gear train 79 located below the conveyors; the pair of chains 74 drives the pair of chains 73 by means of a transmission mechanism 80 located above the conveyors; and the pair of chains 73 drives the pair of chains 72 by means of a step-up gear train 81 located below the conveyors.

As may be seen in FIGS. 12 to 16, the chains 72 to 75 comprise pairs of aligned drive members 84 (FIG. 12). Each drive member 84 consists of a pair of elements 85 in the form of an angle piece which are connected rigidly to one another at a first end 86 and are connected pivotally to the chain at a second end 87 (FIG. 15). A roller 88 is mounted pivotally on the outside face of each element 85 in the form of an angle piece, level with the bent part of the latter. In predetermined sections of the upper portion of each chain 72 to 75, the rollers 88 of a drive member 84 come into engagement with corresponding parallel straight guides 90 (see FIGS. 11 and 15), the effect of this being to cause the drive member 84 to pass from a retracted position, in which it is below the level of the guide rails 67 of the trays 33 (see FIG. 13), into a projecting position (see FIG. 14), in which it can engage into the frame 36 fastened under each tray 33. The position of the drive members 84 on each chain 72 to 75, the synchronization of the chains and the length and arrangement of the straight guides 90 are suitably calculated to ensure that each tray 33 is driven by the chains 72 to 75 at the desired moment and that the trays 33 are grouped correctly, as described below in more detail.

FIG. 11, furthermore, shows diagrammatically the travel-limit detector 65 and the corresponding rod assembly 91 which serves for actuating the roller conveyor 66 of the conveyance sections 15 and 16. The connection between the conveyance sections 16 and 17 which are not at the same level is made by means of a vertical transporter 92 (see FIG. 10) which is provided for picking up a tray 33 arriving at the end of the roller conveyor 66 and for transferring it onto the roller conveyor 97 of the conveyance sections 17 and 18.

The vertical transporter 92, which is arranged in the zone 26 of the containment 6, comprises a motor 93 for conveying the trays 33 vertically, a motor 94 for conveying them horizontally and specific control means 95 for ensuring synchronization with the roller conveyors 66 and 97.

Figure 17A:
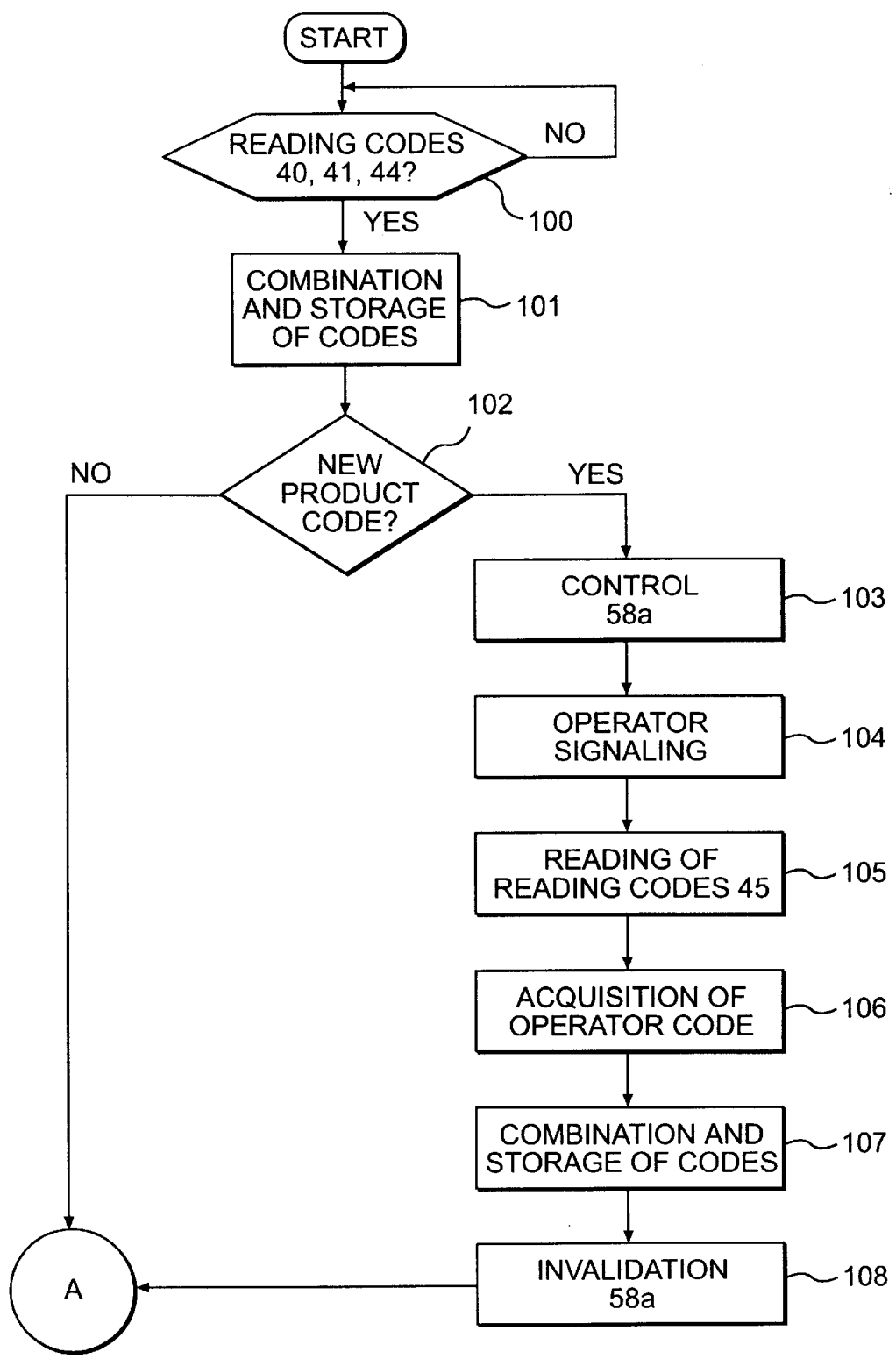
FIGS. 17a and 17b show a block diagram relating to the control functions of the control and monitoring unit.
Figure 17B:
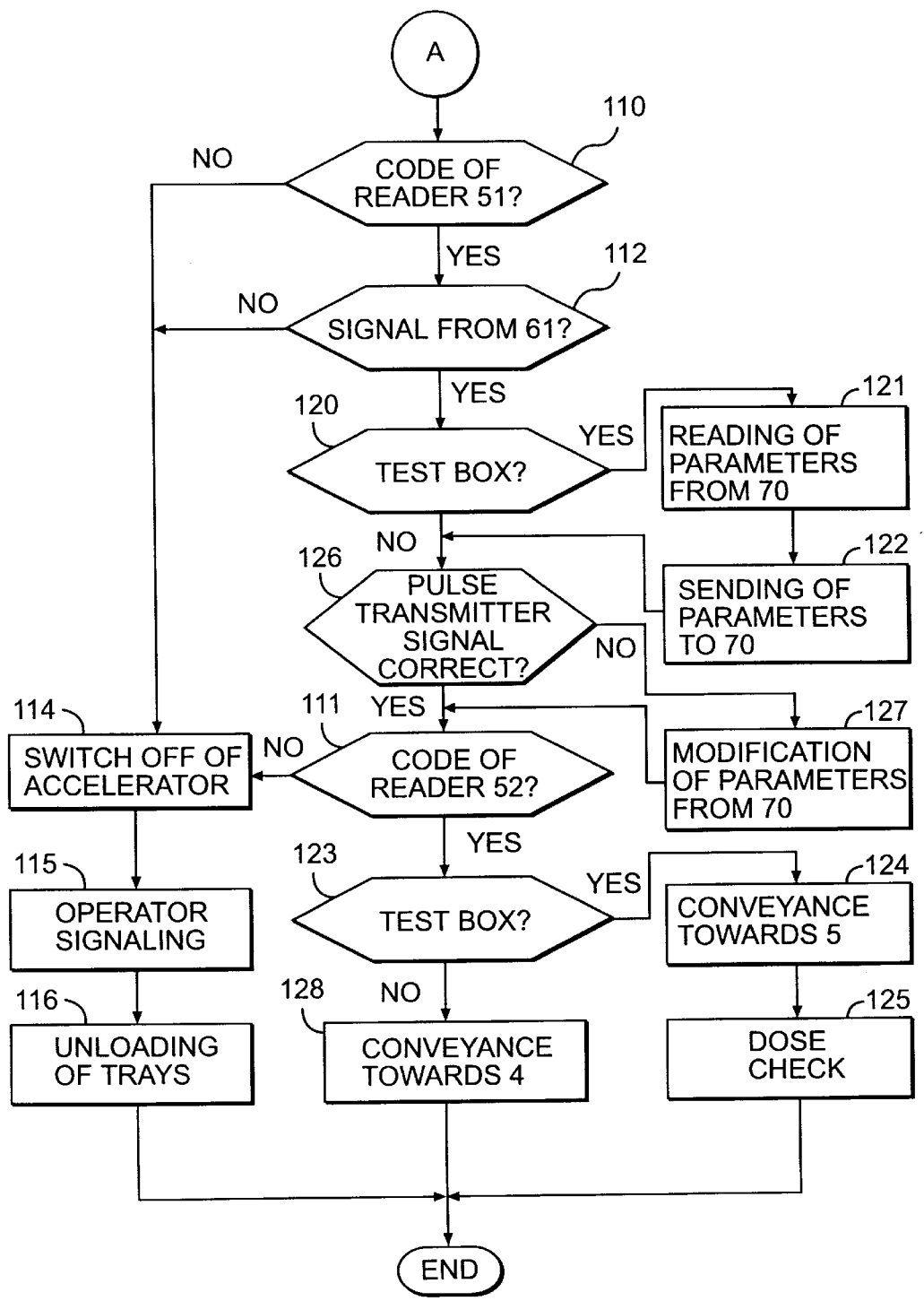

The installation just described functions as follows. At the main loading station 2, the operator places two boxes 31 containing blood lines 30 onto a tray 33, one in front of the other. As illustrated in the flow chart in FIGS. 17a, 17b, the code readers 40, 41 and 44 read the labels 32 and 37 of the boxes 31 and of the tray 33 (block 100) and emit the corresponding signals which are transmitted to the control and monitoring unit 42 which combines (block 101) the data relating to the products and read from the label on the box 31 with the identification number of the tray, read from the label on the tray 33. For the entire time that the boxes 31 dwell inside the installation 1, the said boxes are identified and followed on the conveyance means solely from the identification code of the corresponding tray 33, with which they are combined without any risk of exchange or error: it may be recalled that the conveyance means as a whole are inaccessible to the operators, since the said means are isolated from outside by the metal trelliswork cage 43 and by the containment 6.

Furthermore, the control and monitoring unit 42 checks whether the product code read from the label on the boxes 31 corresponds to that of the previously loaded and processed products (block 102); if not (different products requiring a variation of the processing parameters, such as the intensity of the irradiation generated by the accelerator 70 or the conveying speed of the conveyor 14), the control unit 42 actuates the blocking devices 58a, thus causing the trays 33, already introduced into the main loading station 2, to stop (block 103), and requiring the operator to introduce a test tray 33a at the auxiliary loading station 3 (block 104). For this purpose, suitable signaling means (not shown) may be provided at the station 3. The operator then introduces into the installation a test tray 33a containing devices for controlling the operation. The test tray 33a consists of two test boxes 31a, 31b (FIG. 5), the box 31a arranged first in the direction of travel being empty, and the second box 31b containing means for measuring the irradiation, such as a calorimeter 96. Subsequently, at the operator's command or automatically, after the code of the tray has been read by the reader 45 (block 105), after the operator has depressed an identification code key of the control and monitoring device (block 106) and after the code of the tray and the code introduced manually have been combined (block 107), the blocking devices 58a (block 108) are deactivated by the advance of the tray introduced manually in the auxiliary station 3 and of the test tray 33a and the trays 33 previously loaded at the main loading station 2.

During travel along the conveyance means, the readers 51 and 52 (and, if appropriate, other readers not shown) read the identification code of the trays in order to follow the travel of the transported trays and products along the entire path outside the containment (blocks 110, 111). The information supplied by the readers, the data relating to the synchronization of the motor 55 and, if appropriate, the data supplied by the mechanical travel-limit devices 61, 65 with regard to the interior of the containment 6 (block 112) are used by the control unit 42 in order to locate or identify the exact position of each tray 33 inside the containment accurately at any moment. In the event of an anomaly or when the functioning of the installation is interrupted, the product boxes processed in full, those processed partially and those of which the state is not known perfectly can thus be identified. Furthermore, in the event of a serious anomaly, the control and monitoring unit 42 can stop processing directly by stopping the accelerator 70 (block 114), sending the corresponding error signals to the operator (115) and unloading the trays 33 present on the conveyance means 8 (116).

As mentioned above, the conveyor 62 of the conveyance section 14 is faster than the conveyor 63 (the two parts 63a and 63b of which are displaced at the same speed). The conveyor 62 quickly moves the trays 33 brought by the conveyor 60 away from the latter and causes the trays 33 to be regrouped in the direction of travel, so as to reduce the distance between two successive trays. Furthermore, the start of the guide rails 67 of the trays (the said start not being shown in the figures) and the position of the drive members 84 of the chains 72 are designed in such a way that the drive members come into contact with the lower frame 36 of each tray 33 only when the latter has reached the end of the conveyance section 13, the purpose of this being to prevent the tray 33 from rotating.

The conveyors 62 and 63a are synchronized exactly, in such a way that, when a tray 33 reaches the conveyor 63a, a pair of drive members 84 of the chains 73 engages into the lower frame 36 of the tray 33, after pivoting from the retracted position, shown in FIG. 13, into the projecting position, shown in FIG. 14. The pivoting of the drive members 84 has the effect of imparting to them a horizontal movement which is added to the displacement resulting from the drive by the chains 73; this pivoting therefore causes a slight increase in the speed of the members 84 in relation to the speed of the conveyor 63a. Consequently, at the moment when a tray 33 is driven by the conveyor 63a, this tray undergoes a slight forward push, thus further reducing the distance separating it from the preceding tray (of the order of a few millimeters), without the following tray bumping the one preceding it. The straight guides 90 combined with the conveyor 62 are not as long as this conveyor, so that a tray 33 is released by the conveyor 62, before being driven by the conveyor 63a, and the said tray does not undergo any push despite the difference in speed of the two conveyors.

In the central part of the conveyance section 14, the trays 33 are very close together and travel at a constant speed, thus ensuring uniform irradiation in the irradiation station 7. In this zone, the conveyors 63a, 63b behave in the same way as a single conveyor, since their speeds are equal, and, due to the gap separating them, they are not damaged by irradiation.

When a test tray 33a has been introduced on the conveyance means at the auxiliary loading station 3 (block 120), the control and monitoring unit 42 determines the moment when this tray 33a will reach the irradiation station 7, stores the corresponding processing parameters (block 121) and controls the modification of the irradiation parameters in order to adapt them to the new product to be processed (block 122). Thus, when the test tray 33a reaches the irradiation station 7, the accelerator 70 sets the irradiation parameters at the moment when the first box 31a (empty) passes, and, during the passage of the second box 31b, the calorimeter 96 which the latter contains measures the dose received. The test tray 33a is subsequently unloaded at the auxiliary unloading station 5, and a check is made as to whether the dose received corresponds to the controlled value (blocks 123, 124, 125). A code reader may, if appropriate, be provided at the auxiliary unloading station 5, in order to make it possible to confirm the correct travel of the test trays.

Furthermore, the control and monitoring unit 42 continues to monitor the conveying speed of the trays in the irradiation station 7 by means of a signal sent to the pulse transmitter 56 (block 126), and, if an anomaly occurs in the speed of the motor 55, the said anomaly being capable of being compensated by adjusting the irradiated dose, the said unit controls the modification of the operating parameters of the accelerator 70 (block 127).

After being irradiated in the station 7, the trays 33 are transferred from the conveyor 63b to the conveyor 64, the speed of which has been selected higher than that of the conveyors 63a, 63b, so that processed trays 33 are conveyed quickly towards the end of the conveyance section 14. As soon as the tray 33 reaches the travel limit detector 65, the latter actuates the roller conveyor 66 which drives the tray 33 out of the section 14, without changing its orientation. The conveyor 66 conveys the trays 33 as far as the vertical transporter 92 which picks them up one after the other on the conveyor 66, causes them to descend to the level of the conveyor 97 and transfers them onto the latter.

The trays 33 loaded with irradiated boxes 31 are thus conveyed on the conveyance sections 17–20 below the conveyance sections for the trays loaded with boxes 31 of products to be processed. If they do not contain any test boxes 31a, 31b, the trays are conveyed by means of the conveyors 47, 47b, 47c towards the main unloading station 4 (block 128). There, the reader 38 reads the label 37 of the tray 33 and communicates to the control and processing unit 42 the correct arrival of the trays 33 at the exit of the installation.

The installation described above has the following advantages. It is reliable and efficient, particularly because, in the central part of the section 14, the spaces between the trays are reduced to a few millimeters (thus reducing the idle operating time of the accelerator virtually to zero). Its high performance is attributable, furthermore, to the fact that it makes it possible to modify the irradiation parameters required by different products, without the installation having to be stopped.

The constant conveying speed, particularly in the conveyance section 14, ensures that the irradiation received by the products is uniform and makes it possible to process delicate products, such as PVC blood lines, for which there is a small difference between the admissible maximum and minimum doses for ensuring the sterilization of the products and avoiding damage to them. The monitoring of the entire conveyance, including inside the containment (by means of the pulse transmitter combined with the motor) contributes to ensuring the reliability of the installation and makes it possible to compensate slight speed irregularities, as described above. Moreover, the control and monitoring unit is capable of detecting any anomaly liable to affect sterilization efficiency, of interrupting the processing, and of distinguishing the boxes which have been processed from those which have not been or have been insufficiently processed.

Superposing a plurality of conveyance sections of the products to be processed and for the processed products makes it possible to limit the space occupied by the installation; the use of a vertical transporter makes it possible to reduce the space occupied inside the containment, the manufacturing cost of which is high.

Combining the product boxes 31 with the trays 33 and monitoring, carried out only on the trays inside the installation, make it possible to reduce the periodic checks of the conveyance of the products, even when ambient conditions are not helping the reading of the labels. In fact, the codes printed on the trays may have a better printing quality (thus making reading easier) than the codes printed on the cardboard of the product boxes. Stoppages of the installation which occur as a result of the problem of reading the codes are thus avoided. The presence of the mechanical travel-limit detectors in the critical inner zone 27 and the drive of the trays by means of a catch system which makes the trays 33 integral with the conveyors ensure, on the one hand, the possibility of monitoring the conveyance, even in the critical zone 27, and, on the other hand, safety in the conveyance of the trays. Furthermore, the identification of all the trays and of the boxes which they support is ensured, even when the accelerator is switched off, without the conveyance of the trays being interrupted. Moreover, the inaccessibility of the conveyance means as a whole owing to the trelliswork cage 43 and the containment 6 ensures that it is impossible to change the box/tray combinations established on entry into the installation.

The use of materials resistant to ionizing radiations and the absence of electronic equipment inside the critical zone 27 ensure that the installation functions appropriately and has a long service life. By virtue of all the advantageous characteristics which have just been mentioned, it is possible to reduce the unit cost of processing the products and to subject products having a low unit cost to sterilization by beta-ray irradiation.

The invention is not limited to the embodiments described and illustrated, and it is capable of having variants.

What is claimed is:

1. Method for the sterilization of medical products by irradiation, comprising the steps of:

placing at least one product provided with a product identification code onto a tray provided with a tray identification code;

reading the tray identification code and the product identification code; storing the combination of the tray and product identification codes; conveying the tray along a definite path towards an irradiation station; sterilizing said at least one product at the irradiation station; and locating the tray by reading the tray identification code at definite places along the path.

2. Method according to claim 1, further comprising the steps of:

comparing the read product identification code with the identification code of the product previously stored, and, if the products are not of the same type:

blocking the travel of the tray on which the product is placed;

placing a device for measuring the irradiation dose generated by the irradiation station onto a second tray;

setting the irradiation station so that it emits radiation suitable for sterilizing the product;

conveying the tray towards the irradiation station;

measuring the radiation dose received in the irradiation station by means of the measuring device; and monitoring the measured radiation when the second tray has emerged from the irradiation station.

3. Installation for the sterilization by irradiation of a plurality of medical products, each product having an identification code affixed thereto, the installation comprising:

at least one product loading station;

at least one product unloading station;

an irradiation station located inside a containment having walls capable of stopping sterilizing radiation;

conveyance means for conveying the products to be sterilized from the loading station to the irradiation station and the sterilized products from the irradiation station to the unloading station;

a plurality of trays for supporting the products on the conveyance means, each tray being provided with an identification code;

code-reading means, arranged along the conveyance means, for reading the code affixed to each tray and the code affixed to each product; and control and monitoring means connected to the code-reading means for combining and storing the identification code of each product and the identification code of the tray supporting each product, and for following the travel of the products on the conveyance means.

4. Installation according to claim 3, further comprising mechanical travellimit detection means arranged inside the containment, in order to detect the position of the trays inside the containment and transmit a corresponding signal to the control and monitoring unit.

5. Installation according to claim 3, further comprising code-reading means arranged in the vicinity of the loading station, the control and monitoring means including means for comparing each product introduced in the loading station with a product previously introduced and for controlling a triggering of warning means when these products are not of the same type.

6. Installation according to claim 3, wherein the conveyance means comprises grouping means for grouping the products to be sterilized in the vicinity of the irradiation station.

7. Installation according to claim 3, wherein the grouping means comprises a first conveyor and a second conveyor, the second conveyor being located immediately downstream of the first conveyor in relation to the direction of conveyance of the products and having a conveying speed lower than the conveying speed of the first conveyor.

8. Installation according to claim 7, wherein the first and second conveyors comprise retractable drive members for catching the products and strictly subjecting their displacement to that of the corresponding conveyor.

9. Installation according to claim 7, wherein the second conveyor comprises two half-conveyors separated by a gap located in a zone towards which the irradiation station emits sterilizing radiation.

10. Installation according to claim 7, further comprising a third conveyor located immediately downstream of the second conveyor in relation to the direction of conveyance of the products, the third conveyor having a conveying speed higher than the conveying speed of the second conveyor.

11. Installation according to claim 7, wherein at least the first and second conveyors are chain conveyors, each comprising a pair of chains and in that the drive members each comprise a finger and are mounted pivotably on the chains, so as to be capable of pivoting between a retracted position, in which the finger cannot catch any product, and a projecting position, in which the finger can catch a product.

12. Installation according to claim 7, further comprising means for measuring a speed of the second conveyor, wherein the measuring means is connected to the control and monitoring means, and the control and monitoring means is configured to adjust the irradiation station as a function of the variations in the speed of the conveyor, in such a way that the products receive a predetermined irradiation dose.

13. Installation according to claim 3, wherein the conveyance means comprises superposed conveyance sections, the conveyance sections located at a first level conveying products to be sterilized from the loading station to the irradiation station, and the conveyance sections located at a second level conveying sterilized products from the irradiation station to the unloading station.

14. Installation according to claim 13, wherein the conveyance means comprises a vertical transporter for transferring the products from one conveyance level to another conveyance level.

15. Installation according to claim 1, further comprising a trelliswork cage surrounding the conveyance means outside the containment.

16. A system for sterilizing, by irradiation, a plurality of products, each product having an identification code thereon, and being carried through the system on a carrier, each carrier having an identification code thereon, the system comprising:

at least one product loading station;

at least one product unloading station;

a containment having walls for blocking sterilizing radiation;

an irradiation station located within the containment;

at least one conveyor defining a travel path between the product loading station, the irradiation station and the product unloading station;

at least one carrier code reader arranged along the conveyor, the carrier code reader being configured to detect and read carrier identification codes and for outputting carrier code data;

at least one product code reader arranged along the conveyor and being configured to detect and read product identification codes and for outputting product code data; and a control and monitoring circuit for receiving carrier code data and product code data, for storing in memory an association between specific carriers and product located thereon, and for monitoring travel of the products along said at least one conveyor using carrier code data.

17. The system of claim 16, wherein the control and monitoring circuit is configured to associate particular products with particular trays upstream of the containment and wherein locations of the particular products with the containment are monitored by tracking tray identification codes.

* * * * *

UNITED STATES PATENT AND TRADEMARK OFFICE
CERTIFICATE OF CORRECTION

PATENT NO. : 6,177,677 B1
DATED : January 23, 2001
INVENTOR(S) : Luigi Alboresi and Marco Santi It is certified that error appears in the above-identified patent and that said Letters Patent is hereby corrected as shown below:

<u>Column 11, claim 4,</u>
Line 13, "travellimit" should read -- travel-limit --.

<u>Column 11, claim 7,</u>
Line 28, "claim 3" should read -- claim 6 --.

<u>Column 12, claim 15,</u>
Line 17, "claim 1" should read -- claim 3 --.

Signed and Sealed this

Twentieth Day of November, 2001

*Attest:*

NICHOLAS P. GODICI
*Attesting Officer*     *Acting Director of the United States Patent and Trademark Office*